(12) United States Patent
Dhuppad et al.

(10) Patent No.: US 8,404,727 B2
(45) Date of Patent: *Mar. 26, 2013

(54) PHARMACEUTICAL COMPOSITION THAT INCLUDES A DIPEPTIDYL PEPTIDASE-IV INHIBITOR

(75) Inventors: Ulhas Dhuppad, Maharashtra (IN); Vaijnath Aravat, Maharashtra (IN); Someshwar Navhat, Maharashtra (IN); Abraham Thomas, Navi Mumbai (IN); Suresh Kadam, Maharashtra (IN)

(73) Assignee: Glenmark Pharmaceuticals S.A., La Chaux-de-Fonds (CH)

( * ) Notice: Subject to any disclaimer, the term of this patent is extended or adjusted under 35 U.S.C. 154(b) by 302 days.

This patent is subject to a terminal disclaimer.

(21) Appl. No.: 12/683,696

(22) Filed: Jan. 7, 2010

(65) Prior Publication Data

US 2010/0173964 A1    Jul. 8, 2010

Related U.S. Application Data

(60) Provisional application No. 61/146,847, filed on Jan. 23, 2009.

(30) Foreign Application Priority Data

Jan. 7, 2009    (IN) .............. 45/MUM/2009

(51) Int. Cl.
   *A01N 43/78*    (2006.01)
   *A01N 43/80*    (2006.01)
   *A01N 43/64*    (2006.01)
   *A61K 31/425*    (2006.01)
   *A61K 31/41*    (2006.01)
(52) U.S. Cl. .................. 514/365; 514/372; 514/381
(58) Field of Classification Search ............ 514/365, 514/381

See application file for complete search history.

(56) References Cited

U.S. PATENT DOCUMENTS

| 5,939,560 | A | 8/1999 | Jenkins et al. |
| 6,699,871 | B2 | 3/2004 | Edmondson et al. |
| 2006/0142585 | A1 | 6/2006 | Thomas et al. |
| 2009/0054314 | A1* | 2/2009 | Cruz ........................... 514/12 |

FOREIGN PATENT DOCUMENTS

| EP | 1852108 A1 | 7/2007 |
| WO | 9740832 A1 | 11/1997 |
| WO | 9819998 A2 | 5/1998 |
| WO | 2006040625 A1 | 4/2006 |
| WO | 2008001195 A2 | 1/2008 |

* cited by examiner

Primary Examiner — Sreeni Padmanabhan
Assistant Examiner — Layla Soroush
(74) Attorney, Agent, or Firm — MariaLouisa Lao

(57) ABSTRACT

The present patent application relates to a pharmaceutical composition for oral administration that includes a certain pyrrolidine derivative as DPP-IV inhibitor, and a pharmaceutically acceptable excipient. More particularly, the present invention contemplates pharmaceutical compositions that include melogliptin and a pharmaceutically acceptable excipient as well as to processes for preparing the pharmaceutical composition and the use of the composition in reducing glucose level in a subject. The present invention also contemplates an impurity associated with melogliptin.

9 Claims, No Drawings

PHARMACEUTICAL COMPOSITION THAT INCLUDES A DIPEPTIDYL PEPTIDASE-IV INHIBITOR

PRIORITY DOCUMENT(S)

This patent application claims priority to Indian Provisional Patent Application No. 45/MUM/2009 (filed on Jan. 7, 2009), and under 35 U.S.C. §119(e) to U.S. Provisional Application No. 61/146,847 (filed on Jan. 23, 2009), the contents of each of which are incorporated by reference herein.

TECHNICAL FIELD

The present patent application relates to a pharmaceutical composition that includes dipeptidyl peptidase-IV enzyme ("DPP-IV") inhibitor. Particularly, the present patent application relates to a pharmaceutical composition for oral administration that includes a certain pyrrolidine derivative as DPP-IV inhibitor, and a pharmaceutically acceptable excipient, as well as to processes for preparing the pharmaceutical composition and the use of the composition in reducing glucose level in a subject.

BACKGROUND

Disorders related to increased glucose levels generally refer to a disease process derived from multiple causative factors and characterized, inter alia, by elevated levels of plasma glucose (i.e., hyperglycemia) in the fasting state or after administration of glucose during an oral glucose tolerance test.

Hyperglycemia can be treated with a variety of therapeutic agents for example, peroxisome proliferator-activated receptor active agents, biguanides, alpha-glucosidase inhibitors, and insulin sensitizers. DPP-IV inhibitors have been found to be useful in the treatment of disorders related to increased glucose level, and particularly hyperglycemia. See, for example, PCT application Publications Nos. WO 97/40832 and WO 98/19998, and U.S. Pat. Nos. 5,939,560, and 6,699,871. The usefulness of DPP-IV inhibitors in the treatment of hyperglycemia is believed to be based on the understanding that DPP-IV in vivo inactivates glucagon-like peptide 1 ("GLP-1") and gastric inhibitory peptide ("GIP"). GLP-1 and GIP are incretins and are produced when food is consumed. The incretins stimulate production of insulin. Inhibition of DPP-IV is believed to lead to decreased inactivation of the incretins, and this in turn results in increased effectiveness of incretins in stimulating production of insulin by the pancreas. DPP-IV inhibition is believed to lead to an increased level of serum insulin.

Two of the DPP-IV inhibitors have been approved by the United States FDA, i.e., sitagliptin (JANUVIA® marketed by Merck and Co.) and saxagliptin (ONGLYZA® marketed by Bristol Myers Squibb). Another DPP-IV inhibitor, vildagliptin (GALVUS® marketed by Novartis) is currently commercially available in Europe.

There is a continuing need for new compositions for the treatment of disorders related to increased glucose level and other disorders implicating DPP-IV.

SUMMARY

The present patent application relates to a pharmaceutical composition for oral administration that includes a certain pyrrolidine derivative as DPP-IV inhibitor, and a pharmaceutically acceptable excipient.

The inventors have invented a pharmaceutical composition that includes pyrrolidine derivatives of the formula (A), described below, as a DPP-IV inhibitor, and at least one pharmaceutically acceptable excipient compatible with said compound of the formula (A).

Co-assigned PCT Application Publication No. WO 2006/040625 ("the '625 application"), which is incorporated herein by reference in its entirety and for the purposes stated, describes a novel class of pyrrolidine derivatives (as DPP-IV inhibitors) of the formula (A):

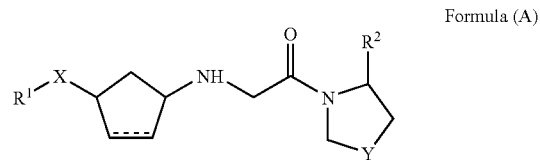

Formula (A)

wherein:
Y is —S(O)$_m$—, —CH$_2$—, CHF, or —CF$_2$;
m is 0, 1, or 2;
X is a bond, C$_1$-C$_5$ alkyl, or —C(=O)—; the dotted line [- - -] in the carbocyclic ring represents an optional bond;
R$^1$ is substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroarylalkyl, —CN, —COOR$^3$, —CONR$^3$R$^4$, —OR$^3$, —NR$^3$R$^4$, or —NR$^3$COR$^4$;
R$^2$ is hydrogen, cyano, COOH, or an isostere of a carboxylic acid (such as SO$_3$H, CONOH, B(OH)$_2$, PO$_3$R$^3$R$^4$, SO$_2$NR$^3$R$^4$, tetrazole, —COOR$^S$, —CONR$^3$R$^4$, —NR$^3$COR$^4$, or —COOCOR$^3$); and
R$^3$ and R$^4$ may be the same or different and are independently hydrogen, nitro, hydroxy, cyano, formyl, acetyl, halogen, substituted or unsubstituted amino, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroarylalkyl or a substituted or unsubstituted carboxylic acid derivative;
or a pharmaceutically acceptable prodrug thereof, pharmaceutically acceptable N-oxide thereof, or pharmaceutically acceptable salt thereof.

Inter alia, the '625 application discloses (2S,4S)-1-{2-[(3S,1R)-3-(1H-1,2,4-triazol-1-ylmethyl)cyclopentylamino]acetyl}-4-fluoropyrrolidine-2-carbonitrile (INN: Melogliptin). The present invention particularly contemplates pharmaceutical compositions that include melogliptin (including its salts, analogs, derivatives, polymorphs, solvates, single isomers, enantiomers and mixtures thereof) and a pharmaceutically acceptable excipient.

Glucose level reducing properties of melogliptin mesylate and/or structurally related compounds have been described in the '625 application, which is incorporated herein by reference for the specific purpose stated.

Surprisingly, the inventors found that melogliptin mesylate is not compatible with some well-accepted pharmaceutical excipients. Formulating the pharmaceutical compositions that contain melogliptin with such incompatible excipients may yield unstable and pharmaceutically unacceptable products. Hence, the inventors of the present invention specifically contemplate formulating the pharmaceutical compositions described herein with excipients compatible with melogliptin or its salts.

Thus, in an embodiment, the present invention provides a pharmaceutical composition that includes an admixture of melogliptin or its salt, and at least one pharmaceutically acceptable excipient compatible with melogliptin or its salt. Preferably, the melogliptin salt is melogliptin mesylate.

In the context of present invention, the pharmaceutically acceptable excipients compatible with melogliptin or its salts include but are not limited to mannitol, starch, xylitol, maltodextrin, hydroxypropyl methylcellulose, hydroxypropyl cellulose, ethyl cellulose, microcrystalline cellulose, silicified microcrystalline cellulose, dicalcium phosphate anhydrous, glyceryl behenate, triethyl citrate, polyethylene glycol, croscarmellose sodium, stearic acid, talc, hydrogenated cottonseed oil, magnesium stearate, colloidal silicon dioxide, polysorbate, sodium lauryl sulfate, and mixtures thereof.

Further, the inventors of the present invention have surprisingly discovered that formulating the pharmaceutical compositions of melogliptin with such incompatible excipients yields an impurity, 7-fluoro-1-imino-2-[3-(1H-1,2,4-triazol-1-ylmethyl)cyclopentyl] hexahydropyrrolo[1,2-a]pyrazin-4(1H)-one mesylate (i.e., "impurity A").

Impurity A

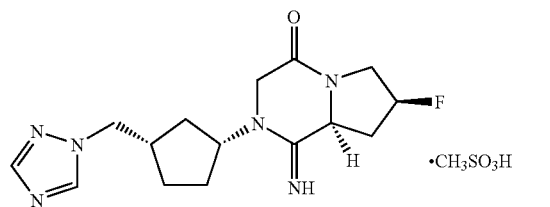

In yet another embodiment, the present patent application also relates to the process of preparation of a compound 7-fluoro-1-imino-2-[3-(1H-1,2,4-triazol-1-ylmethyl)cyclopentyl] hexahydropyrrolo[1,2-a]pyrazin-4(1H)-one mesylate.

In yet another embodiment, the present patent application relates to a stable pharmaceutical composition for oral administration that includes melogliptin, and at least one pharmaceutically acceptable excipient compatible with melogliptin, wherein the pharmaceutical composition remains stable when stored at temperature of about 40° C. and relative humidity of about 75% for at least 3 months.

In another embodiment, the present invention provides a pharmaceutical composition for oral administration that includes an admixture of melogliptin or its salt, and a pharmaceutically acceptable excipient, wherein the composition contains not more than about 1%, or preferably not more than 0.5% w/w, of an impurity 7-fluoro-1-imino-2-[3-(1H-1,2,4-triazol-1-ylmethyl)-cyclopentyl]hexahydropyrrolo[1,2-a]pyrazin-4(1H)-one mesylate, when stored at a temperature of about 40° C. and a relative humidity of about 75% for at least 3 months. Preferably, the melogliptin salt is melogliptin mesylate and the excipient is selected from mannitol and dicalcium phosphate anhydrous.

Another embodiment provides a pharmaceutical composition for oral administration that includes melogliptin or its salt, and at least one pharmaceutically acceptable excipient compatible with melogliptin, wherein the amount of melogliptin ranges from about 10 mg to about 300 mg, or from about 25 mg to about 200 mg.

In another embodiment, the present invention relates to a method of reducing an increased glucose level in a mammal, the method comprises orally administering to the mammal an effective amount of a pharmaceutical composition that includes an admixture of melogliptin or its salt, and at least one pharmaceutically acceptable excipient compatible with melogliptin or its salt. Preferably, the mammal is human.

In the context of present invention, the effective amount of the pharmaceutical composition comprises about 10 mg to about 300 mg, or preferably about 25 mg to about 200 mg of melogliptin or its salt.

The present invention also relates to a process for preparing a pharmaceutical composition for oral administration, wherein the process includes admixing melogliptin or its salt, and at least one pharmaceutically acceptable excipient compatible with melogliptin or its salt. Preferably, the process includes dry blending, direct compression or dry co-granulation of melogliptin and a pharmaceutically acceptable excipient compatible with melogliptin.

The present invention also relates to a method of testing the purity of a pharmaceutical composition comprising melogliptin or its salt wherein the method comprises assaying the said composition for the presence of (7-fluoro-1-imino-2-[3-(1H-1,2,4-triazol-1-ylmethyl)cyclopentyl] hexahydro-pyrrolo[1,2-a]pyrazin-4(1H)-one mesylate.

DETAILED DESCRIPTION

The terms used herein are defined as follows. If a definition set forth in the present application and a definition set forth in an earlier-filed provisional application to which the present application claims priority are in conflict, the definition in the present application shall control the meaning of the terms.

The term "effective amount" denotes an amount of an active ingredient that, when administered to a subject for treating a state, disorder or condition, produces an intended therapeutic benefit in a subject.

The term "active ingredient" (used interchangeably with "active" or "active substance") used herein includes melogliptin, or its salts, analogs, derivatives, polymorphs, solvates, single isomers, enantiomers, metabolites, prodrugs and mixtures thereof.

By "salts" or "pharmaceutically acceptable salts", it is meant those salts and esters which are, within the scope of sound medical judgment, suitable for use in contact with the tissues of humans and lower animals without undue toxicity, irritation, and allergic response, commensurate with a reasonable benefit to risk ratio, and effective for their intended use. Representative acid addition salts include the hydrochloride, hydrobromide, sulphate, bisulphate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, and lauryl sulphate salts. Representative alkali or alkaline earth metal salts include the sodium, calcium, potassium and magnesium salts. In a preferred embodiment, the melogliptin salt is melogliptin mesylate.

The term "treating" or "treatment" as used herein also covers the "prophylaxis", "mitigation", "prevention", "amelioration", or "suppression" of a disorder related to increased glucose level in a subject.

The term "mammal" includes human and other animals, such as domestic animals (e.g., household pets including cats and dogs) and non-domestic animals (such as wildlife). Preferably, the mammal is a human.

As set forth above, the present invention provides a pharmaceutical composition for oral administration that includes:
(a) a compound of the formula (A), and
(b) at least one pharmaceutically acceptable excipient compatible with said compound of the formula (A).

Preferably, the compound of the formula (A) is (2S,4S)-1-{2-[(3S,1R)-3-(1H-1,2,4-triazol-1-ylmethyl)cyclopentylamino]acetyl}-4-fluoropyrrolidine-2-carbonitrile (INN: Melogliptin) and its salts; more preferably, melogliptin mesylate. Preferably, the dose of melogliptin in the composition ranges from about 10 mg to about 300 mg, or from about 25 mg to about 200 mg for administration by oral route.

Thus, in an embodiment, the present invention provides a pharmaceutical composition that includes an admixture of melogliptin or its salt, and at least one pharmaceutically acceptable excipient compatible with melogliptin or its salt.

As set forth above, the pharmaceutical composition described herein includes at least one excipient compatible with melogliptin. As set forth above, it has been surprisingly discovered that many traditional pharmaceutical excipients are not compatible with melogliptin, namely may cause significant decomposition of melogliptin when intimately mixed and co-formulated therewith. Such excipients that are not compatible with melogliptin include calcium carbonate, crospovidone, povidone, xanthan gum, methyl cellulose, sodium starch glycolate, propylene glycol, tartaric acid, disodium hydrogen phosphate, dibasic calcium phosphate dihydrate, sodium metabisulfite, and lactose monohydrate.

Non-limiting examples of pharmaceutically acceptable excipients compatible with melogliptin include such diluents as mannitol, starch, xylitol, maltodextrin, hydroxypropylmethyl cellulose, hydroxypropyl cellulose, ethyl cellulose, microcrystalline cellulose, silicified microcrystalline cellulose, dicalcium phosphate anhydrous, and glyceryl behenate; such plasticizers as triethyl citrate and polyethylene glycol; such disintegrants as croscarmellose sodium; such lubricants/glidants as stearic acid, talc, hydrogenated cottonseed oil and magnesium stearate, colloidal silicon dioxide; and such surfactants as polysorbate and sodium lauryl sulfate; and mixtures thereof.

The degradation of melogliptin can be evaluated by increase in the impurity/related substance ("RS") upon storage. In the context of present invention, a pharmaceutically acceptable excipient is deemed to be compatible with melogliptin when no more than about 0.5% w/w of impurity A is generated when said pharmaceutically acceptable excipient is co-formulated or intimately mixed/admixed with melogliptin in certain ratios by weight, and stored at a temperature of about 40° C. for about 4 weeks period as per the compatibility study exemplified in Example 1.

In yet another embodiment, the present patent application relates to a stable pharmaceutical composition for oral administration that includes melogliptin or its salts, and at least one pharmaceutically acceptable excipient compatible with melogliptin or its salts, wherein the pharmaceutical composition remains stable when stored at temperature of about 40° C. and relative humidity of about 75% for at least 3 months.

In the context of present invention, pharmaceutical composition is deemed to be stable when not more than about 1% w/w of impurity A is generated, when said pharmaceutical composition is stored at a temperature of about 40° C. and a relative humidity of about 75% for at least 3 months.

Thus, in another embodiment, the present invention provides a pharmaceutical composition for oral administration that includes an admixture of melogliptin or its salt, and a pharmaceutically acceptable excipient, wherein the composition contains not more than about 1% w/w, or preferably not more than 0.5% w/w, of an impurity 7-fluoro-1-imino-2-[3-(1H-1,2,4-triazol-1-ylmethyl)-cyclopentyl]hexahydropyrrolo[1,2-a]pyrazin-4(1H)-one mesylate, when stored at a temperature of about 40° C. and a relative humidity of about 75% for at least 3 months. Preferably, the melogliptin salt is melogliptin mesylate and the excipient is selected from mannitol and dicalcium phosphate anhydrous.

For getting marketing approval for a new drug product, regulatory authority requires that the pharmaceutical composition remains stable during its normal shelf life. Submissions made to regulatory authorities therefore typically include analytical data which demonstrate that impurities are or are present only at a negligible level, during the shelf-life of the drug product. The impurities which may appear on storage include substances resulting from degradation of the active agent.

In an embodiment, the amount of melogliptin or its salt in the pharmaceutical composition ranges from about 10 mg to about 300 mg, or from about 25 mg to about 200 mg.

The pharmaceutical compositions may be in conventional forms, for example, tablets, capsules, granules (synonymously, "beads" or "particles" or "pellets"), suspensions, emulsions, powders, dry syrups, and the like. The capsules may contain granule/pellet/particle/mini-tablets/mini-capsules containing the active ingredient.

As set forth above, the pharmaceutical composition for oral administration may include diluents such as microcrystalline cellulose ("MCC"), silicified MCC (e.g., PROSOLV™), microfine cellulose, lactose, starch, pregelatinized starch, mannitol, sorbitol, dextrates, dextrin, maltodextrin, dextrose, calcium carbonate, calcium sulfate, dibasic calcium phosphate dihydrate, tribasic calcium phosphate, magnesium carbonate, magnesium oxide and the like; cores/beads such as insoluble inert materials like glass particles/beads or silicon dioxide, calcium phosphate dihydrate, dicalcium phosphate, calcium sulfate dihydrate, microcrystalline cellulose, cellulose derivatives; soluble cores such as spheres of sugars like dextrose, lactose, mannitol, starches, sorbitol, or sucrose; insoluble inert plastic materials such as spherical or nearly spherical core beads of polyvinyl chloride, polystyrene or any other pharmaceutically acceptable insoluble synthetic polymeric material, and the like or mixtures thereof; binders or adherents such as acacia, guar gum, alginic acid, dextrin, maltodextrin, methylcellulose, ethyl cellulose, hydroxyethyl cellulose, hydroxypropyl cellulose (e.g., KLUCEL®), low substituted hydroxypropyl cellulose, hydroxypropyl methylcellulose (e.g., METHOCEL®), carboxymethyl cellulose sodium, povidone (various grades of KOLLIDON®, PLASDONE®), starch and the like; disintegrants such as carboxymethyl cellulose calcium, croscarmellose sodium, (e.g., Ac-Di-Sol®, PRIMELLOSE®), crospovidone (e.g., KOLLIDON®, POLYPLASDONE®), povidone K-30, polacrilin potassium, starch, pregelatinized starch, sodium starch glycolate (e.g., PRIMOGEL, EXPLOTAB®), and the like; plasticizers such as acetyltributyl citrate, phosphate esters, phthalate esters, amides, mineral oils, fatty acids and esters, glycerin, triacetin or sugars, fatty alcohols, polyethylene glycol, ethers of polyethylene glycol, fatty alcohols such as cetostearyl alcohol, cetyl alcohol, stearyl alcohol, oleyl alcohol, myristyl alcohol and the like. Solvents that may be used in granulation or layering include water, methanol, ethanol, isopropyl alcohol, acetone, methylene chloride, dichloromethane, and the like and mixtures thereof.

Pharmaceutical formulations described herein may further include any one or more of pharmaceutically acceptable glidants and lubricants like stearic acid, magnesium stearate, talc, colloidal silicon dioxide, sodium stearyl fumarate, opacifiers, colorants, and other commonly used carriers. Suitable preservatives include, by way of example and without limitation, phenoxyethanol, parabens such as methyl paraben and propyl paraben and their sodium salts, propylene glycols, sorbates, urea derivatives such as diazolindinyl urea, and the like and mixtures thereof. Suitable buffering agents include, by way of example and without limitation, sodium hydroxide, potassium hydroxide, ammonium hydroxide and the like and mixtures thereof. Suitable chelating agents include mild agents, such as, for example, ethylenediaminetetraacetic acid ("EDTA"), disodium edetate and EDTA derivatives, and the like and mixtures thereof.

Suitable polymers include, by way of example and without limitation, those known to one of ordinary skill in the art such as gum arabic, sodium based lignosulfonate, methyl methacrylate, methacrylate copolymers, isobutyl methacrylate, and ethylene glycol dimethacrylate.

Suitable gelling agents/viscosifying agents include, by way of example and without limitation, carbomers (CARBOPOL), modified cellulose derivatives, naturally-occurring, synthetic or semi-synthetic gums such as xanthan gum, acacia and tragacanth, sodium alginate, gelatin, modified starches, cellulosic polymers such as hydroxypropyl cellulose, hydroxyethyl cellulose, hydroxypropyl methylcellulose, hydroxypropyl methylcellulose phthalate, and methyl cellulose; co-polymers such as those formed between maleic anhydride and methyl vinyl ether, colloidal silica and methacrylate derivatives, polyethylene oxides, polyoxyethylene-polyoxypropylene copolymers, polyvinyl alcohol and the like and mixtures thereof.

The pharmaceutical composition described herein may further comprise surfactants. Examples of such surfactants include, but are not limited to, poloxamer, polyoxyethylene sorbitan esters (known as POLYSORBATE or TWEEN), polyethoxylated castor oil (CREMOPHOR), methyl glucose sesquistearate, PEG-20 methyl glucoside sesquistearate, Steareth-21, polyethylene glycol 20 sorbitan monostearate, polyethylene glycol 60 sorbitan monostearate, polyethylene glycol 80 sorbitan monostearate, Steareth-20, Ceteth-20, PEG-100 stearate, sodium stearoyl sarcosinate, hydrogenated lecithin, sodium cocoylglyceryl sulfate, sodium stearyl sulfate, sodium stearoyl lactylate, PEG-20 glyceryl monostearate, sucrose monostearate, sucrose polystearates, polyglyceryl 10 stearate, polglceryl 10 myristate, steareth 10, DEA oleth 3 phosphate, DEA oleth 10 phosphate, PPG-5 Ceteth 10 phosphate sodium salt, PPG-5 Ceteth 10 phosphate potassium salt, steareth-2, PEG-5 soya sterol oil, PEG-10 soya sterol oil, diethanolamine cetyl phosphate, sorbitan monostearate, diethylene glycol monostearate, glyceryl monostearate, and the like and mixtures thereof.

The pharmaceutical composition described herein may further contain one or more suitable solvents. Examples of such solvents include, but are not limited to, water; tetrahydrofuran; propylene glycol; liquid petrolatum; ether; petroleum ether; alcohols, e.g., methanol, ethanol, isopropyl alcohol and higher alcohols; aromatics, e.g., benzene and toluene; alkanes, e.g., pentane, hexane and heptane; ketones, e.g., acetone and methyl ethyl ketone; chlorinated hydrocarbons, e.g., chloroform, carbon tetrachloride, methylene chloride and ethylene dichloride; acetates, e.g., ethyl acetate; lipids, e.g., isopropyl myristate, diisopropyl adipate and mineral oil and the like and mixtures thereof.

In another embodiment, the present invention relates to a method of reducing an increased glucose level in a mammal, the method comprises orally administering to the mammal an effective amount of a pharmaceutical composition that includes an admixture of melogliptin or its salt, and at least one pharmaceutically acceptable excipient compatible with melogliptin or its salt. Preferably, the mammal is human.

The present invention also relates to a process for preparing a pharmaceutical composition for oral administration, wherein the process includes admixing melogliptin or its salt, and at least one pharmaceutically acceptable excipient compatible with melogliptin or its salt. Preferably, the process includes dry blending, direct compression or dry co-granulation of melogliptin and a pharmaceutically acceptable excipient compatible with melogliptin.

In an embodiment, the pharmaceutical composition for oral administration described herein may be prepared by, such processes as dry blending, direct compression or dry co-granulation.

For example, the process for making the pharmaceutical composition may include (1) granulating the active ingredient along with the compatible pharmaceutically acceptable excipient so as to obtain granulate, and (2) converting the granulate into suitable dosage forms for oral administration. The typical processes involved in the preparation of the pharmaceutical compositions include various unit operations such as mixing, sifting, solubilizing, dispersing, granulating, lubricating, compressing, coating, and the like. These processes, as contemplated by a person skilled in the formulation art, have been incorporated herein for preparing the pharmaceutical compositions of the present invention.

The present invention also relates to a process for preparing 7-fluoro-1-imino-2-[3-(1H-1,2,4-triazol-1-ylmethyl)-cyclopentyl]hexahydropyrrolo[1,2-a]pyrazin-4(1H)-one mesylate ("impurity A") wherein the process comprises, heating (2S, 4S)-1-{2-[(3S,1R)-3-(1H-1,2,4-triazol-1-ylmethyl)cyclopentylamino]acetyl}-4-fluoropyrrolidine-2-carbonitrile mesylate at 150-160 C for 3 to 4 h.

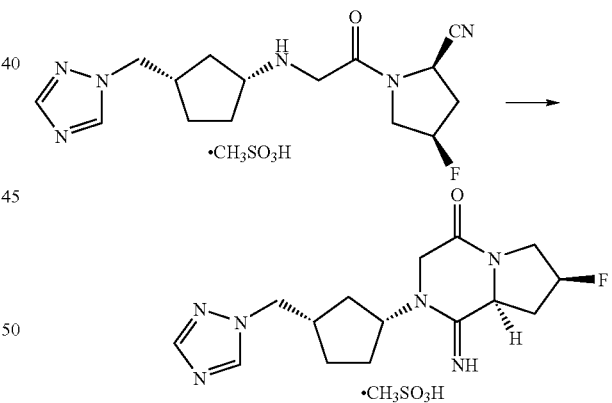

In yet another embodiment, the present invention also provides a process for preparing 7-fluoro-1-imino-2-[3-(1H-1,2,4-triazol-1-ylmethyl)-cyclopentyl]hexahydro-pyrrolo[1,2-a]pyrazin-4(1H)-one mesylate ("impurity A") wherein the process comprises refluxing (2S,4S)-1-{2-[(3S,1R)-3-(1H-1,2,4-triazol-1-ylmethyl)cyclopentylamino]acetyl}-4-fluoropyrrolidine-2-carbonitrile mesylate in an appropriate solvent (e.g., acetonitrile) under basic conditions (e.g., triethylamine).

The present invention also relates to a method of testing the purity of a pharmaceutical composition comprising melogliptin or its salt wherein the method comprises assaying the said composition for the presence of (7-fluoro-1-imino-2-[3-

(1H-1,2,4-triazol-1-ylmethyl)cyclopentyl] hexahydro-pyrrolo[1,2-a]pyrazin-4(1H)-one mesylate.

It will be understood that various modifications may be made to the embodiments disclosed herein. Therefore the above description should not be construed as limiting, but merely as exemplifications of preferred embodiments. Other arrangements and methods may be implemented by those skilled in the art without departing from the scope and spirit of this invention.

The following examples are provided to enable one skilled in the art to practice the invention and are merely illustrative of the invention. The examples should not be read as limiting the scope of the invention.

EXAMPLES

Example 1

Compatibility Study of Melogliptin with Various Excipients

Melogliptin Mesylate was Subjected for Compatibility Studies in Solid State Condition with Dry Mixing Technique Using the Following Protocol:

Melogliptin mesylate and various excipients in predetermined w/w ratios were mixed geometrically. Melogliptin mesylate to excipients ratios were selected based on the excipients concentration expected to be used during the development of the formulation. The placebo of each excipient used was kept on respective stability conditions as control.

The samples were stored in glass vials. The vials were closed with rubber stoppers and sealed with aluminum seals, and kept in upright position.

The vials were stored at three storage conditions: 25° C., 30° C. and 40° C.

The samples were analyzed initially, then followed by the end of 1 week, 2 weeks and 4 weeks time periods for related substances (RS), as monitored by HPLC and differential scanning calorimetry (DSC), to study the interaction between melogliptin and various excipients.

The compatibility data in terms of RS generated initially and upon 4 weeks ("4 W") storage at about 40° C. of various samples are tabulated below.

| S. No. | Excipient | Melogliptin mesylate:Excipient ratio (% w/w) | RS (% w/w) by HPLC Impurity A Initial | RS (% w/w) by HPLC Impurity A 4 W | RS (% w/w) by HPLC Total RS Initial | RS (% w/w) by HPLC Total RS 4 W |
|---|---|---|---|---|---|---|
| 1 | Melogliptin mesylate | 1:0 | 0.02 | 0.05 | 0.12 | 0.13 |
| 2 | Microcrystalline cellulose (Avicel PH 101) | 1:1 | 0.03 | 0.03 | 0.14 | 0.13 |
| 3 | Lactose monohydrate | 1:5 | 0.01 | 0.79 | 0.10 | 0.97 |
| 4 | Lactose anhydrous (Pharmatose DCL21) | 1:5 | 0.01 | 0.37 | 0.08 | 0.56 |
| 5 | Dicalcium phosphate anhydrous | 1:05 | 0.04 | 0.10 | 0.13 | 0.20 |
| 6 | Dibasic calcium phosphate dihydrate | 1:1 | 0.03 | 0.65 | 0.12 | 0.77 |
| 7 | Starch | 1:1 | 0.01 | 0.09 | 0.10 | 0.32 |
| 8 | Mannitol | 1:5 | 0.01 | 0.46 | 0.09 | 0.60 |
| 9 | HPMC (E5) | 1:0.2 | 0.03 | 0.04 | 0.15 | 0.15 |
| 10 | HPC (Klucel LF) | 1:0.5 | 0.02 | 0.09 | 0.15 | 0.20 |
| 11 | Stearic acid | 1:0.01 | 0.03 | 0.06 | 0.15 | 0.16 |
| 12 | Magnesium stearate | 1:0.01 | 0.02 | 0.07 | 0.13 | 0.18 |
| 13 | Glyceryl behenate (Compritol 888 ATO) | 1:0.5 | 0.02 | 0.07 | 0.11 | 0.19 |
| 14 | Purified talc | 1:0.1 | 0.03 | 0.04 | 0.13 | 0.12 |
| 15 | Croscarmellose sodium (Ac-di-sol) | 1:0.2 | 0.01 | 0.11 | 0.12 | 0.53 |
| 16 | Sodium starch glycolate | 1:1 | 0.02 | 1.79 | 0.11 | 1.95 |
| 17 | Propylene glycol | 1:0.1 | 0.04 | 1.57 | 0.13 | 1.68 |
| 18 | Polysorbate 80 | 1:0.1 | 0.02 | 0.04 | 0.13 | 0.13 |
| 19 | Triethyl citrate | 1:0.1 | 0.01 | 0.05 | 0.11 | 0.16 |
| 20 | Sodium lauryl sulphate | 1:0.05 | 0.02 | 0.05 | 0.11 | 0.13 |
| 21 | Sodium meta bisulphite | 1:0.2 | — | 0.69 | 0.08 | 0.95 |
| 22 | Polyethylene glycol (PEG 6000) | 1:0.1 | 0.03 | 0.10 | 0.12 | 0.23 |
| 23 | Disodium hydrogen phosphate anhydrous | 1:0.2 | 0.60 | 28.9 | 0.69 | 38.9 |
| 24 | Calcium carbonate | 1:1 | 2.15 | 10.76 | 3.23 | 19.84 |
| 25 | Crospovidone | 1:0.5 | 0.04 | 0.74 | 0.25 | 1.04 |
| 26 | Xylitol | 1:1 | 0.05 | 0.06 | 0.25 | 0.32 |
| 27 | Hydrogenated cottonseed oil (Rylo TG 11) | 1:1 | 0.02 | 0.03 | 0.26 | 0.32 |
| 28 | Xanthan gum | 1:1 | 0.04 | 1.07 | 0.19 | 1.94 |
| 29 | Methyl cellulose | 1:1 | 0.13 | 1.48 | 0.34 | 2.08 |
| 30 | Maltodextrin | 1:1 | — | 0.19 | 0.21 | 0.42 |
| 31 | Povidone | 1:1 | 0.18 | 4.05 | 0.35 | 5.01 |
| 32 | Tartaric acid | 1:1 | — | 5.29* | 0.06 | 5.80* |

*Data upon 2 weeks storage.

Brief Analytical Method for Determination of RS in Melogliptin Mesylate:

A reversed-phase gradient HPLC method was developed. The analysis was performed using C18 HPLC column (Phenomenex Gemini 110 A, C-18, 50×4.6 mm, 3 µm). The mobile phase was a gradient mixture of a solution of 1.26 g of ammonium formate in 1000 ml of purified water adjusted to pH 8.4 using 25% v/v ammonia solution (Mobile Phase A) and a solution of 1.26 g of ammonium formate in a mixture of purified water (800 ml) and acetonitrile (200 ml) adjusted to pH 8.4 using 25% v/v ammonia solution (Mobile Phase B). The gradient program is provided below. The flow rate was 1.0 ml/min; injection volume 20 µl; and column temperature was 25° C. Suitable dilutions of the placebo, standard and test samples were injected in the column. Areas for impurity A (eluted at the relative retention time of 0.51) and total RS in the chromatogram were integrated, and accordingly the contents of impurity A and total RS were determined.

Gradient Program:

| Time (min) | Mobile Phase A (%) | Mobile Phase B (%) |
|---|---|---|
| 0.01 | 100 | 0.0 |
| 2 | 100 | 0.0 |
| 27 | 40 | 60 |
| 32 | 30 | 70 |
| 50 | 30 | 70 |
| 50.1 | 100 | 0.0 |
| 55 | 100 | 0.0 |

Examples 2-5

Pharmaceutical Tablet Compositions Containing Melogliptin Mesylate and Pharmaceutically Acceptable Excipients Compatible with Melogliptin

| | Composition (mg/tablet) | | | |
|---|---|---|---|---|
| Ingredients | Example 2 | Example 3 | Example 4 | Example 5 |
| Melogliptin mesylate | 134.0 | 134.0 | 134.4 | 134.4 |
| Silicified MCC (Prosolv HD 90) | — | — | — | 64.6 |
| Stearic acid | 0.67 | — | 0.65 | 1.0 |
| Talc | — | 13.4 | — | — |
| COATING | | | | |
| HPMC E5 LV | — | — | Weight gain 2.5% w/w | — |
| Opadry OY-C-7000A* | Weight gain 3.5% w/w | Weight gain 3.5% w/w | Weight gain 3.5% w/w | Weight gain 3.5% w/w |
| Isopropyl alcohol# | q.s. | q.s. | q.s. | q.s. |
| Dichloromethane# | q.s. | q.s. | q.s. | q.s. |

*Commercially available from Colorcon Inc.
Evaporate during process.

Manufacturing Processes

Example 2

Melogliptin mesylate was compacted in a roller compactor. The compacts obtained were passed through ASTM Sieve # 20 to obtain granules. The granules thus obtained were lubricated by adding stearic acid and mixing. The lubricated granules were compressed into tablets. The tablets were coated with the dispersion of Opadry OY-C-7000A in isopropyl alcohol and dichloromethane.

Example 3

Melogliptin mesylate was compacted in a roller compactor. The compacts obtained were passed through ASTM Sieve # 20 to obtain granules. The granules thus obtained were lubricated by adding talc and mixing. The lubricated granules were compressed into tablets. The tablets were coated with the dispersion of Opadry OY-C-7000A in isopropyl alcohol and dichloromethane.

Example 4

Melogliptin mesylate was compacted in a roller compactor. The compacts obtained were passed through ASTM Sieve # 20 to obtain granules. The granules thus obtained were lubricated by adding stearic acid and mixing. The lubricated granules were compressed into tablets. The tablets were seal-coated with HPMC E5 LV followed by dispersion of Opadry OY-C-7000A in isopropyl alcohol and dichloromethane.

Example 5

Melogliptin mesylate was compacted in a roller compactor. The compacts obtained were passed through ASTM Sieve # 20 to obtain granules. The granules thus obtained were lubricated by adding silicified MCC and stearic acid and blending. The lubricated granules were compressed into tablets. The tablets were coated with the dispersion of Opadry OY-C-7000A in isopropyl alcohol and dichloromethane.

Examples 6-9

Tablet Compositions Containing Melogliptin Mesylate

| | Composition (mg/tablet) | | | |
|---|---|---|---|---|
| Ingredients | Example 6 | Example 7 | Example 8 | Example 9 |
| Melogliptin mesylate | 270.0 | 135.0 | 130.0 | 65.0 |
| Mannitol | 7.2** | — | 102.8** | 51.4** |
| Dicalcium phosphate anhydrous | — | 61.0 | — | — |
| Stearic acid | 2.8 | 4.0 | 7.2 | 3.6 |
| COATING | | | | |
| Opadry OY-C-7000A* | Weight gain 3.5% w/w | Weight gain 3.5% w/w | Weight gain 2.0% w/w | Weight gain 2.0% w/w |
| Isopropyl alcohol# | q.s. | q.s. | q.s. | q.s. |
| Dichloromethane# | q.s. | q.s. | q.s. | q.s. |

*Commercially available from Colorcon Inc.
**Pearlitol SD 200.
Evaporate during process.

Manufacturing Processes

Example 6

Melogliptin mesylate was compacted in a roller compactor. The compacts obtained were passed through ASTM Sieve # 20 to obtain granules. The granules were blended with mannitol and lubricated by adding stearic acid and mixing. The lubricated granules were compressed into tablets and were coated with the dispersion of Opadry OY-C-7000A in isopropyl alcohol and dichloromethane.

Example 7

Melogliptin mesylate and dibasic calcium phosphate anhydrous were blended and granulated with purified water. The wet granules were dried in a fluidized bed drier and the dried granules were sized through ASTM Sieve # 30 to obtain sized granules. The sized granules were lubricated by adding stearic acid and blending. The lubricated granules were compressed into tablets. The tablets were coated with the dispersion of Opadry OY-C-7000A in isopropyl alcohol and dichloromethane.

Example 8 and Example 9

Melogliptin mesylate and mannitol were compacted in a roller compactor and the compacts obtained were passed through ASTM Sieve # 20 to obtain granules. The granules were lubricated by adding stearic acid and blending. The lubricated granules were compressed into tablets on a rotary compression machine and the tablets were coated with the dispersion of Opadry OY-C-7000A in isopropyl alcohol and dichloromethane.

Example 10

Stability Data of Examples 2-9

Stability Pack Sealed HDPE container
Storage condition: Temperature of about 40° C. and about 75% relative humidity for 3 months (3 M).

| Composition | Stability data by HPLC | | | | | |
|---|---|---|---|---|---|---|
| | Impurity A (% w/w) | | Total Impurities (% w/w) | | Assay (% w/w) | |
| Example | Initial | 3 M | Initial | 3 M | Initial | 3 M |
| Example 2 | — | 0.09 | 0.35 | 0.55 | 96.8 | 96.4 |
| Example 3 | 0.02 | 0.24 | 0.38 | 0.72 | 97.9 | 98.6 |
| Example 4 | 0.03 | 0.13 | 0.39 | 0.59 | 98.1 | 100.1 |
| Example 5 | 0.03 | 0.35 | 0.38 | 0.77 | 97.3 | 99.1 |
| Example 6 | 0.02 | 0.06 | 0.15 | 0.21 | 100.7 | 101.5 |
| Example 7 | 0.02 | 0.12 | 0.33 | 0.42 | 101.2 | 102.7 |
| Example 8 | 0.01 | 0.04 | 0.11 | 0.12 | 98.5 | 100.4 |
| Example 9 | — | 0.05 | 0.11 | 0.13 | 100.2 | 99.3 |

Brief Analytical Method:

The tablets were powdered and powder equivalent to 200 mg of melogliptin mesylate was extracted with 100 ml of a diluent [mixture of water:acetonitrile (90:10 v/v)]. The extract was subjected to analysis for impurities.

A) Impurities:

A reversed-phase gradient HPLC method was developed. The analysis was performed using C18 HPLC column (Phenomenex Gemini 110 A, C-18, 50×4.6 mm, 3 μm). The mobile phase was a gradient mixture of a solution of 1.26 g of ammonium formate in 1000 ml of purified water adjusted to pH 8.4 using 25% v/v ammonia solution (Mobile Phase A) and a solution of 1.26 g of ammonium formate in a mixture of purified water (800 ml) and acetonitrile (200 ml) adjusted to pH 8.4 using 25% v/v ammonia solution (Mobile Phase B). The gradient program is provided below. The flow rate was 1 ml/min; injection volume of 20 μl; and column temperature of 25° C. Suitable dilutions of the placebo, standard and test samples were injected in the column. Areas for impurity A (eluted at the relative retention time of 0.51) and total RS in the chromatogram were integrated, and accordingly the contents of impurity A and total RS was determined.

Gradient Program:

| Time (min) | Mobile Phase A (%) | Mobile Phase B (%) |
|---|---|---|
| 0.01 | 100 | 0.0 |
| 2 | 100 | 0.0 |
| 27 | 40 | 60 |
| 32 | 30 | 70 |
| 50 | 30 | 70 |
| 50.1 | 100 | 0.0 |
| 55 | 100 | 0.0 |

The method was subjected to system suitability test and the following are the results:

| | Relative retention time | Limit of detection | Limit of quantification | Retention factor |
|---|---|---|---|---|
| Melogliptin mesylate | 1.0 | 0.0029% | 0.0088% | — |
| Impurity A | 0.51 | 0.0032% | 0.0099% | 0.75 |

B) Assay:

The tablets were powdered and powder equivalent to 200 mg of melogliptin mesylate was extracted with 100 ml of a diluent [mixture of water:methanol (75:25) adjusted to pH 2.0 with orthophosphoric acid] The extract was subjected to analysis for assay.

A reversed-phase isocratic HPLC method was developed. The analysis was performed using C18 HPLC column (Inertsil ODS −3V, 250×4.6 mm, 5μ). The mobile phase was a mixture of buffer and methanol (75:25% v/v). The buffer consisted of 8.709 g of dipotassium hydrogen phosphate in about 800 ml of water adjusted to pH 7.5 with orthophosphoric acid and diluted to 1000 ml with purified water. The flow rate was 1.5 ml/min; injection volume was 20 μl; and column temperature was 25° C. Suitable dilutions of the standard and test samples were injected in the column and the areas of the standard and test in the chromatogram were integrated and the assay in percent was determined.

Example 11

Compound of 7-fluoro-1-imino-2-[3-(1H-1,2,4-triazol-1-ylmethyl)cyclopentyl] hexahydropyrrolo[1,2-a]pyrazin-4(1H)-one

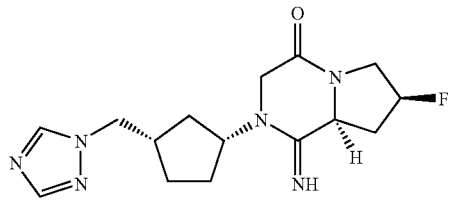 [SMILES: N=C1[C@@H]2C[C@H](F)CN2C(=O)CN1[C@@H]1CC[C@H](Cn2cncn2)C1]

The compound, 7-fluoro-1-imino-2-[3-(1H-1,2,4-triazol-1-ylmethyl)cyclopentyl] hexahydropyrrolo[1,2-a]pyrazin-4(1H)-one has MP 158-162° C.; IR (KBr) 3435, 2973, 2323, 1672, 1652, 1447, 1431, 1275, 1010 cm$^{-1}$; $^1$H NMR (300 MHz, DMSO-d$_6$) δ 1.30-1.38 (m, 1H), 1.58-1.70 (m, 2H), 1.80-2.00 (m, 3H), 2.19-2.29 (m, 1H), 2.46-2.56 (m, 1H), 2.64-2.78 (m, 1H), 3.77-3.87 (m, 3H), 4.00 (d, J=16.2 Hz, 1H), 4.18 (dd, J=2.4, 4.5 Hz, 2H), 4.40 (dd, J=4.8, 6.3 Hz, 1H), 4.80-4.94 (m, 1H), 5.23 (s, 0.5 H), 5.39 (s, 0.5 H), 7.94 (s, 1H), 8.06 (s, 1H); ESI-MS (m/z) 321 (100%, M+H)+.

Example 12

Preparation of 7-fluoro-1-imino-2-[3-(1H-1,2,4-triazol-1-ylmethyl)cyclopentyl] hexahydropyrrolo[1,2-a]pyrazin-4(1H)-one mesylate

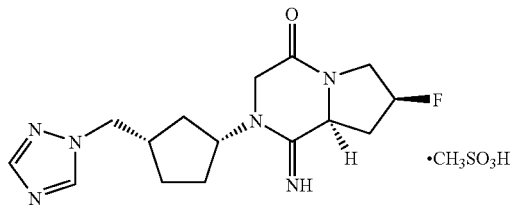

(2S,4S)-4-fluoro-1-({[(1R,3S)-3-(1H-1,2,4-triazol-1-ylmethyl)-cyclopentyl]amino}acetyl)pyrrolidine-2-carbonitrile mesylate salt was melted at 150-160° C. for 3 to 4 h and the residue was cooled to 25-30° C. To this, a mixture of methanol (100 ml, 2 vol.) and ethyl acetate (250 ml, 5 vol.) was added and heated at 50-55° C. The reaction mixture on cooling to 25-30° C. precipitates 7-fluoro-1-imino-2-[(3S,1R)-3-(1H-1,2,4-triazol-1-ylmethyl)cyclopentyl]-perhydroazolo[1,2-a]pyrazin-4-one mesylate. $^1$H NMR (300 MHz, DMSO-$d_6$) δ 1.52-1.88 (m, 6H), 2.21-2.40 (m, 5H), 2.77-2.80 (m, 1H), 3.52-3.83 (m, 2H), 3.95-4.00 (d, 1H), 4.18-4.25 (m, 3H), 4.42 (m, 1H), 4.85 (m, 1H), 5.39-5.56 (d, 1H), 7.98 (s, 1H), 8.54 (s, 1H), 9.17 (s, 2H); ESI-MS (m/z) 321 (100%); $^{13}$C NMR (300 MHz, DMSO-$d_6$) δ 27.00, 26.71, 32.04, 35.81, 32.54, 37.74, 39.97, 47.06, 51.85, 51.54, 52.80, 56.02, 57.73, 92.12, 89.82, 144.14, 151.43, 161.74, 162.12.

All publications, patents, and patent applications cited in this application are herein incorporated by reference to the same extent as if each individual publication, patent, or patent application was specifically and individually indicated to be incorporated herein by reference.

We claim:

1. A pharmaceutical composition for oral administration comprising melogliptin or its salt and a pharmaceutically acceptable excipient selected from mannitol and dicalcium phosphate anhydrous, wherein the composition contains not more than 1% w/w of (7-fluoro-1-imino-2-[3-(1H-1,2,4-triazol-1-ylmethyl)cyclopentyl]hexahydropyrrolo [1,2-a] pyrazin-4(1H)-one mesylate, after being stored at a temperature of about 40 ° C. and a relative humidity of about 75% for 3 months or more.

2. The pharmaceutical composition according to claim 1, wherein the melogliptin salt is melogliptin mesylate.

3. The pharmaceutical composition according to claim 1, further comprises a pharmaceutically acceptable excipient selected from starch, xylitol, maltodextrin, hydroxypropyl cellulose, ethyl cellulose, silicified microcrystalline cellulose, glyceryl behenate, triethyl citrate, polyethylene glycol, stearic acid, talc, hydrogenated cottonseed oil, polysorbate, sodium lauryl sulfate, and mixtures thereof.

4. The pharmaceutical composition according to claim 1, which comprises from about 0.003% to about 0.5% w/w of (7-fluoro-1-imino-2-[3-(1H-1,2,4-triazol-1-ylmethyl)cyclopentyl] hexahydropyrrolo[1,2-a]pyrazin-4(1H)-one mesylate.

5. A pharmaceutical composition for oral administration comprising from about 10 mg to about 300 mg of melogliptin mesylate and a pharmaceutically acceptable excipient selected from mannitol and dicalcium phosphate anhydrous, and optionally further comprising starch, xylitol, maltodextrin, hydroxypropyl cellulose, ethyl cellulose, silicified microcrystalline cellulose, glyceryl behenate, triethyl citrate, polyethylene glycol, stearic acid, talc, hydrogenated cottonseed oil, polysorbate, sodium lauryl sulfate, and mixtures thereof, wherein the composition further comprises from about 0.003% to about 0.5% w/w of (7-fluoro-1-imino-2-[3-(1H-1,2,4-triazol-1-ylmethyl) cyclopentyl] hexahydro-pyrrolo[1,2-a]pyrazin-4(1H)-one mesylate, when stored at a temperature of about 40° C. and a relative humidity of about 75% for at least 3 months.

6. The pharmaceutical composition according to claim 1, wherein the melogliptin or its salt is present in an amount of about 10 mg to about 300 mg.

7. The pharmaceutical composition according to claim 1, wherein the melogliptin or its salt is present in an amount of about 25 mg to about 200 mg.

8. The pharmaceutical composition according to claim 5, wherein the melogliptin mesylate is present in an amount of about 25 mg to about 200 mg.

9. A pharmaceutical composition for oral administration comprising from about 10 mg to about 300 mg of melogliptin mesylate and a pharmaceutically compatible excipient selected from a group consisting of mannitol and dicalcium phosphate anhydrous, wherein the composition comprises not more than 1% w/w of (7-fluoro-1-imino-2-[3-(1H-1,2,4-triazol-1-ylmethyl) cyclopentyl] hexahydropyrrolo[1,2-a] pyrazin-4(1H)-one mesylate, when stored at a temperature of about 40° C. and a relativehumidity of about 75% for at least 3 months.

* * * * *